(12) United States Patent
Zhou et al.

(10) Patent No.: US 10,748,277 B2
(45) Date of Patent: Aug. 18, 2020

(54) TISSUE CHARACTERIZATION BASED ON MACHINE LEARNING IN MEDICAL IMAGING

(71) Applicants: Siemens Healthcare GmbH, Erlangen (DE); The Johns Hopkins University, Baltimore, MD (US)

(72) Inventors: Shaohua Kevin Zhou, Plainsboro, NJ (US); David Liu, Franklin Park, NJ (US); Berthold Kiefer, Erlangen (DE); Atilla Peter Kiraly, Plainsboro, NJ (US); Benjamin L. Odry, West New York, NY (US); Robert Grimm, Nuremberg (DE); Li Pan, Perry Hall, MD (US); Ihab Kamel, Ellicott City, MD (US)

(73) Assignees: Siemens Healthcare GmbH, Erlangen (DE); The Johns Hopkins University, Baltimore, MD (US)

( * ) Notice: Subject to any disclaimer, the term of this patent is extended or adjusted under 35 U.S.C. 154(b) by 644 days.

(21) Appl. No.: 15/261,124

(22) Filed: Sep. 9, 2016

(65) Prior Publication Data
US 2018/0075597 A1 Mar. 15, 2018

(51) Int. Cl.
*G06T 7/00* (2017.01)
*G06N 20/00* (2019.01)
(Continued)

(52) U.S. Cl.
CPC ............ *G06T 7/0012* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS 9,177,104 B2 * 11/2015 Madabhushi ......... G06T 7/0014
9,262,583 B2 * 2/2016 Madabhushi ......... G06T 7/0014
(Continued)

FOREIGN PATENT DOCUMENTS

| WO | WO0131580 | 5/2001 |
| WO | WO2015042421 | 3/2015 |

(Continued)

OTHER PUBLICATIONS

Brain Tumor Segmentation Using Convolutional Neural Networks in MRI Images; PEreira et akl; Mar. 4, 2016.*
(Continued)

*Primary Examiner* — Nancy Bitar

(57) ABSTRACT

Tissue is characterized using machine-learnt classification. The prognosis, diagnosis or evidence in the form of a similar case is found by machine-learnt classification from features extracted from frames of medical scan data. The texture features for tissue characterization may be learned using deep learning. Using the features, therapy response is predicted from magnetic resonance functional measures before and after treatment in one example. Using the machine-learnt classification, the number of measures after treatment may be reduced as compared to RECIST for predicting the outcome of the treatment, allowing earlier termination or alteration of the therapy.

18 Claims, 5 Drawing Sheets

(51) Int. Cl.
    G06K 9/46       (2006.01)
    G16H 30/40      (2018.01)
    G06T 11/00      (2006.01)
    G16H 50/20      (2018.01)
    A61B 5/055      (2006.01)
    A61B 6/03       (2006.01)
    A61B 8/08       (2006.01)
    G16H 50/70      (2018.01)

(52) U.S. Cl.
    CPC .............. *A61B 8/08* (2013.01); *G06K 9/4671* (2013.01); *G06N 20/00* (2019.01); *G16H 50/20* (2018.01); *G06T 11/003* (2013.01); *G06T 2207/10072* (2013.01); *G06T 2207/20081* (2013.01); *G16H 30/40* (2018.01); *G16H 50/70* (2018.01)

(56) References Cited

U.S. PATENT DOCUMENTS

| | | | | |
|---|---|---|---|---|
| 9,275,456 | B2* | 3/2016 | Mori | A61B 5/0013 |
| 9,739,783 | B1* | 8/2017 | Kumar | G01N 33/6893 |
| 10,521,911 | B2* | 12/2019 | Odry | G16H 30/40 |
| 2013/0202173 | A1* | 8/2013 | Buckler | G06T 7/12 |
| | | | | 382/131 |
| 2014/0294272 | A1* | 10/2014 | Madabhushi | G01R 33/5608 |
| | | | | 382/131 |
| 2015/0087957 | A1* | 3/2015 | Liu | G06K 9/6214 |
| | | | | 600/408 |
| 2015/0213302 | A1* | 7/2015 | Madabhushi | G06K 9/00147 |
| | | | | 382/133 |
| 2017/0091937 | A1* | 3/2017 | Barnes | G06K 9/6228 |
| 2017/0116387 | A1* | 4/2017 | El-Zehiry | G16H 50/30 |
| 2019/0021677 | A1* | 1/2019 | Grbic | G06K 9/6267 |

FOREIGN PATENT DOCUMENTS

| | | |
|---|---|---|
| WO | WO2015048103 | 4/2015 |
| WO | WO2017023569 | 2/2017 |

OTHER PUBLICATIONS

Siamese Neural Networks for One-Shot Image Recognition by Gregory Koch ( http://www.cs.toronto.edu/~gkoch/files/msc-thesis.pdf ) May 2015.*

Bonekamp, Susanne, et al. "Unresectable hepatocellular carcinoma: MR imaging after intraarterial therapy. Part I. Identification and validation of volumetric functional response criteria." Radiology 268.2 (2013): 420-430.

Bonekamp, Susanne, et al. "Unresectable hepatocellular carcinoma: MR imaging after intraarterial therapy. Part II. Response stratification using volumetric functional criteria after intraarterial therapy." Radiology 268.2 (2013): 431-439.

Chopra, Sumit, Raia Hadsell, and Yann LeCun. "Learning a similarity metric discriminatively, with application to face verification." 2005 IEEE Computer Society Conference on Computer Vision and Pattern Recognition (CVPR'05). vol. 1. IEEE, 2005.

Eisenhauer, EA1, et al. "New response evaluation criteria in solid tumours: revised RECIST guideline (version 1.1)." European journal of cancer 45.2 (2009): 228-247.

Li, Zhen, et al. "Islet cell liver metastases: assessment of volumetric early response with functional MR imaging after transarterial chemoembolization." Radiology 264.1 (2012): 97-109.

European Search Report dated Jan. 25, 2018 in corresponding European application No. 17189559.2.

* cited by examiner

TISSUE CHARACTERIZATION BASED ON MACHINE LEARNING IN MEDICAL IMAGING

BACKGROUND

The present embodiments relate to tissue characterization in medical imaging.

Magnetic resonance images are widely used in medical diagnosis and therapy. For example, magnetic resonance is used for breast tumor diagnosis following the guidelines of the Breast Imaging-Reporting and Data System (BIRADS), which are based on clinically descriptive tags like mass (shape, margin, mass enhancement), symmetry or asymmetry, non-mess-like enhancement in an area that is not a mass (distribution modifiers, internal enhancement), kinetic curve assessment, and other findings. Similarly for prostate, the Prostate Imaging and Reporting and Data System (PIRADS) specifies the clinically descriptive tags for special prostate regions, such as peripheral zone, central zone, and transition zone. For liver tissue characterization, fibrosis staging is possible based on reading of the magnetic resonance images. Similar approaches are used in other imaging modalities, such as ultrasound, computed tomography, positron emission tomography, or single photon emission computed tomography.

To assess therapy, multimodal magnetic resonance scans are acquired before and after therapy. A simple morphological (e.g., size-based) scoring is commonly performed in tumor treatment assessment, such as the Response Evaluation Criteria in Solid Tumors (RECIST) criteria. The assessment of treatment response is critical in determining the course of continuing treatment since chemotherapy drugs may have adverse effects on the patient. In basic clinical settings, treatment assessment is done morphologically with tumor size. Due to this simple approach, it can take longer to determine if a treatment is succeeding.

The decision to stop therapy may occur earlier by employing functional magnetic resonance information than with the RECIST criteria. For example, treatment effectiveness may be determined earlier by using image-based functional measurements, such as intensity based histograms of the functional measures. These histogram-based intensity values are manually analyzed in clinical practice and may not necessarily capture subtleties related to image texture and local dissimilarity that may better represent cell density, vasculature, necrosis, or hemorrhage characteristics important to clinical diagnosis.

BRIEF SUMMARY

By way of introduction, the preferred embodiments described below include methods, systems, instructions, and non-transitory computer readable media for tissue characterization in medical imaging. Tissue is characterized using machine-learnt classification. The prognosis, diagnosis or evidence in the form of a similar case is found by machine-learnt classification from features extracted from frames of medical scan data with or without external data such as age, gender, and blood biomarkers. The texture or other features for tissue characterization may be learned using deep learning. Using the features, therapy response is predicted from magnetic resonance functional measures before and after treatment in one example. Using the machine-learnt classification, the number and time between measures after treatment may be reduced as compared to RECIST for predicting the outcome of the treatment, allowing earlier termination or alteration of the therapy.

In a first aspect, a method is provided for tissue characterization in medical imaging. A medical scanner scans a patient where the scanning provides multiple frames of data representing a tissue region of interest in the patient. A processor extracts values for features from the frames of data. A machine-learnt classifier implemented by the processor classifies a therapy response of the tissue of the tissue region from the values of the features as input to the machine-learnt classifier. The therapy response is transmitted.

In a second aspect, a method is provided for tissue characterization in medical imaging. A medical scanner scans a patient where the scanning provides different frames of data representing different types of measurements for tissue in the patient. A processor extracts values for features from the frames of data. A machine-learnt classifier implemented by the processor classifies the tissue of the patient from the values of the features as input to the machine-learnt classifier. The tissue classification is transmitted.

In a third aspect, a method is provided for tissue characterization in medical imaging. A patient is scanned with a medical scanner where the scanning provides a frame of data representing a tumor in the patient. A processor extracts values for deep-learnt features from the frame of data. A deep-machine-learnt classifier implemented by the processor classifies the tumor from the values of the features as input to a machine-learnt classifier. The classification of the tumor is transmitted.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In advanced image analytics, complex features, such as image texture, are automatically found and included in an automated format capable of being employed in clinical use cases. Using machine-learnt classification to interrogate the image has the potential to extract texture and/or other image-based information for classification in clinical use cases. A generic pipeline and user interface is capable of finding and processing complex features from medical image data.

Several approaches for tumor prognosis and outcomes allow such analytics along with an interface to make the analytics readily accessible to physicians and support staff. The first approach uses robust image textural and/or other image features extracted by the computer as a feature set for further analysis. The second approach uses a deep learning pipeline involving a Siamese network to automatically create and classify features in a parallel convolutional network for the same patient at two different time points and/or different types of measures. The deep learning network and interface are provided for image analytics for lesion and/or tissue characterization and therapy prediction.

In one embodiment for tumor prognosis, diagnosis or finding of similar cases, a series of features is extracted from multiple image contrasts and/or multiple examination timepoints. The textural and/or other image features are used in a classifier. A Siamese deep-learning neural network may be used to identify the features. Non-image data, such blood test results age, gender, or blood serum biomarkers, may also be used as features. The extracted features are computed against each other using a machine-learnt classifier to determine the diagnosis, prognosis, or find similar cases. For finding similar cases, the images from the similar cases are obtained from a database of previously document cases. The previously documented cases are used to determine the reference case or cases. The diagnosis, prognosis, or finding of similar cases may be performed via a cloud based service that delivers results.

For the user interface, a user marks the tumor of interest in one or more images of a time series, possibly with a single click, and the computer produces the diagnosis, prognosis, or similar cases report in response. This clinical product and interface may minimize interaction. The single click per image assists in segmentation and/or more precise identification of regions. By only requiring a single click or region designation in the pre and post treatment images, the interaction is minimized, increasing the clinical feasibility of the approach. The output report may include clinical evidence, in the form of numbers (e.g., quantifying the textural features that lead to the decision) or in the form of references to previous clinical cases. A single-click interface determines results, allowing for a clinically feasible approach to incorporate complex image features into tumor prognosis and therapy.

Figure 1:
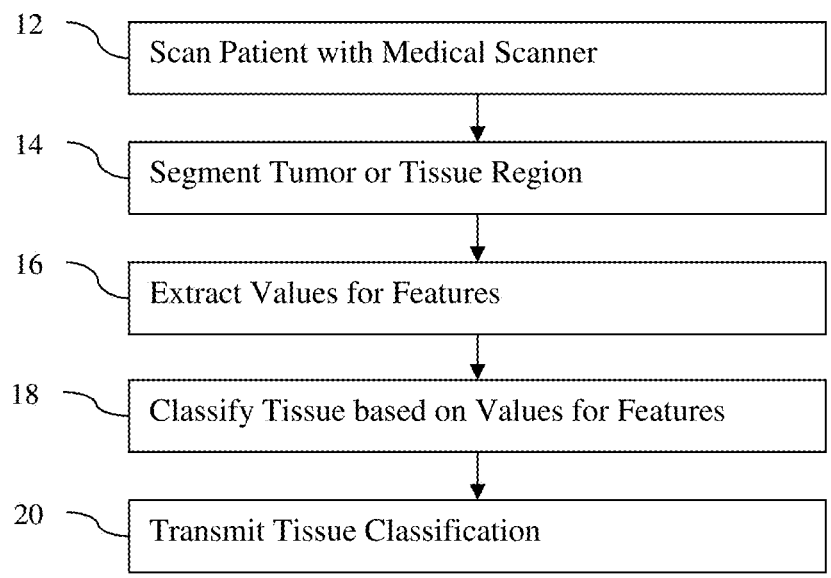
FIG. 1 is a flow chart diagram of one embodiment of a method for characterizing tissue in medical imaging.

FIG. 1 shows one embodiment of a flow chart of a method for tissue characterization in medical imaging. For tissue characterization, such as tumor type, tumor response to treatment, identification of similar tumors in other patients, tumor prognosis, or tumor diagnosis, a machine-learnt classifier is applied. The machine-learnt classifier uses information from one or more frames of data to classify the tumor. Frames of data from different times or different types of measures may be used to classify. In one approach, the features extracted from the frames as the information are manually defined. In another approach, deep learning identifies the features that best characterize the tumor. The features learned with deep learning may be texture and/or non-texture, such as features from the frame or clinical data.

The acts are performed in the order shown (e.g., top to bottom) or other orders. Additional, different, or fewer acts may be provided. For example, the method is performed without transmitting the classification in act 20. As another example, the segmentation of act 14 is not performed, instead the classification is applied to the entire frame of data.

In act 12, one or more medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format. As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for imaging, such as scan data representing the patient.

Any type of medical image may be used. In one embodiment, magnetic resonance frames of data representing a patient are acquired. Magnetic resonance data is acquired by scanning with a magnetic resonance system. Using an imaging sequence, the magnetic resonance system scans the patient. Data representing an interior region of a patient is acquired. The magnetic resonance data is k-space data. Fourier analysis is performed to reconstruct the data from the k-space into a three-dimensional object or image space, providing the frame of data. In other embodiments, x-ray, computed tomography, ultrasound, positron emission tomography, single photon emission computed tomography, or other medical imaging scanner scans the patient. Combination scanners, such as magnetic resonance and positron emission tomography or computed tomography and positron emission tomography systems may be used to scan. The scan results in a frame of data acquired by the medical imaging scanner and provided directly for further processing or stored for subsequent access and processing.

The frame of data represents a one, two, or three-dimensional region of the patient. For example, the multi-dimensional frame of data represents an area (e.g., slice) or volume of the patient. Values are provided for each of multiple locations distributed in two or three dimensions. A tumor or suspicious tissue within the patient is represented by the values of the frame of data.

The frame of data represents the scan region at a given time or period. The dataset may represent the area or volume over time, such as providing a 4D representation of the patient. Where more than one frame is acquired, the different frames of data may represent the same or overlapping region of the patient at different times. For example, one or more frames of data represent the patient prior to treatment, and one or more frames of data represent the patient after treatment or interleaved with on-going treatment.

Where more than one frame is acquired, the different frames may represent different contrasts. For example, different types of contrast agents are injected or provided in the patient. By scanning tuned to or specific to the different types of contrast, different frames of data representing the different contrast agents are provided.

Where more than one frame is acquired, the different frames may represent different types of measures (multi-modal or multi-parametric frames of data). By configuring the medical scanner, different types of measurements of the tissue may be performed. For example in magnetic resonance, both anatomical and functional measurements are performed. As another example in magnetic resonance, different anatomical or different functional measurements are performed. For different anatomical measurements, T1 and T2 are two examples. For different functional measurements, apparent diffusion coefficient (ADC), venous perfusions, and high B-value are three examples. In one embodiment, a T2 frame of data and an ADC frame of data are computed (e.g., different b-value images are acquired to compute a frame of ADC data). Frames of data from different types of scanners may be used.

A combination of different times and types of measures may be used. For example, one set of frames of data represents different types of measures (e.g., T2 and ADC) for pre-treatment, and another set of frames of data represent the same different types of measures (e.g., T2 and ADC) for post-treatment. Multi-dimensional and multi-modal image data is provided for each time. In other embodiments, a single frame of data representing just one type of measure for one time is acquired by scanning.

Where multiple frames represent the tissue at different times, the frames are spatially registered. The registration removes translation, rotation, and/or scaling between the frames. Alternatively, registration is not used.

In act 14, the tissue of interest is identified. The tissue of interest is identified as a region around and/or including the tumor. For example, a box or other shape that includes the tumor is located. Alternatively, the tissue of interest is identified as tissue representing the tumor, and the identified tumor tissue is segmented for further analysis.

The identification is performed by the user. The user, using a user input (e.g., mouse, trackball, keyboard, buttons, sliders, and/or touch screen), identifies the tissue region to be used for feature extraction, classification, and transmission of the classification results. For example, the user selects a center of the tumor about which a processor places a box or other region designator. The user may size or position a region designator with or without center selection. In other approaches, the user indicates a location on the suspicious tissue, and the processor segments the suspicious tissue based on the user placed seed. Alternatively, a processor automatically identifies the tissue region of interest without user selection.

Figure 2:
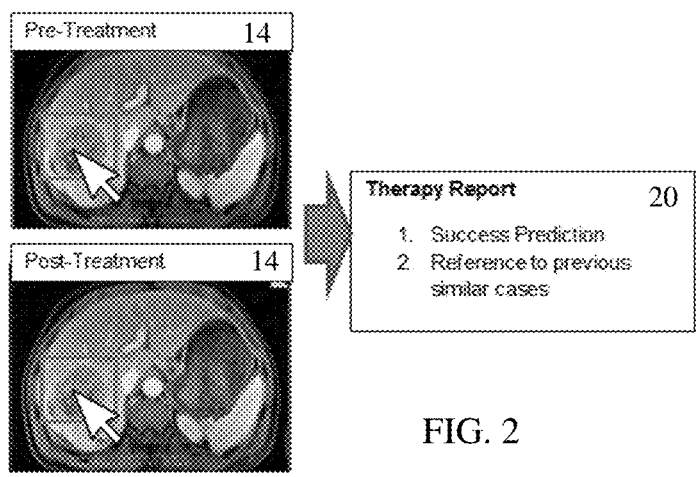
FIG. 2 represents user interaction for tissue characterization according to one embodiment.

FIG. 2 shows an example graphic user interface or approach with minimal user interaction for tissue characterization. In the example of FIG. 2, the classification is for reporting on therapy. Two images corresponding to two frames of data at two times are provided, one pre-treatment and one post-treatment. Given both the pre and post treatment image sets, the user clicks on the tumor center (represented by the arrow tip) in each time point. A bounding box centered at the user selected point is placed, designating the tissue region of interest.

In response to the selection, the computer then returns the predicted success of treatment in an automated report. The report may also contain diagnosis of similar cases that have been previously reviewed in a database as references. The treatment outcome or other classification is determined via a single-click on each image or frame of data without the need to perform any manual and/or automatic segmentation. A "single-click" or simple user input is provided for tumor diagnosis, treatment planning, and/or treatment response assessment. The same approach and technology can be used in any medical imaging product that examines tumor prognosis and treatment based on data acquired from a scanner.

The tumor tissue with or without surrounding tissue is segmented. The data is extracted from the frame for further processing. The pixel or voxel values for the region of interest are isolated. Alternatively, the locations in the region are flagged or marked without being separated from other locations in the frame of data.

In act 16 of FIG. 1, a processor extracts values for features. The processor is part of the medical imaging scanner, a separate workstation, or a server. In one embodiment, the processor extracting the values is a server remote from the medical scanner, such as a server in the cloud. A manufacturer of the medical scanner or a third party provides classification as a service, so the frames of data are communicated through a computer network to the server for extraction of the features and classification from the extracted values.

Values for any number of features are extracted from the frame or frames of data. The values for a texture of the tissue represented by at least one of the frames of data are extracted. The texture of the tissue is represented by the measures of the frame of data. The extraction of the values for each feature is performed for the tissue region of interest, avoiding application to other tissue outside the region of interest. Alternatively, the values for other regions outside the region of interest are extracted.

Each feature defines a kernel for convolution with the data. The results of the convolution are a value of the feature. By placing the kernel at different locations, values for that feature at different locations are provided. Given one feature, the values of that feature at different locations are calculated. Features for other texture information than convolution may be used, such as identifying a maximum or minimum. Other features than texture information may be used.

In one embodiment, the features are manually designed. The feature or features to be used are pre-determined based on a programmer's experience or testing. Example features include scaled invariant feature transformation, histogram of oriented gradients, local binary pattern, gray-level co-occurrence matrix, Haar wavelets, steerable, or combinations thereof. A feature extraction module computes features from images to better capture essential subtleties related to cell density, vasculature, necrosis, and/or hemorrhage that are important to clinical diagnosis or prognosis of tissue.

Figure 3:
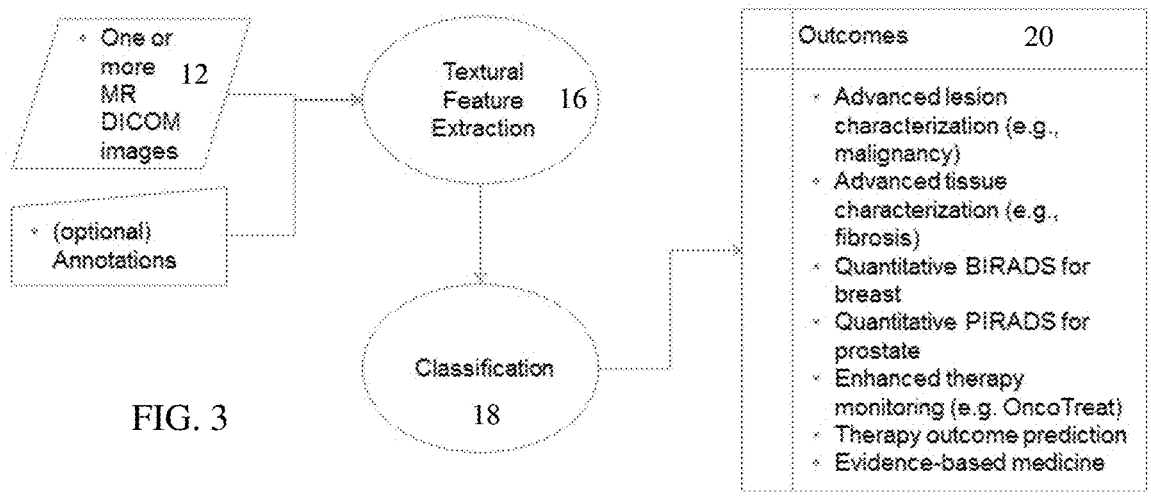
FIG. 3 is a flow chart diagram of a machine-learnt classifier embodiment of the method for characterizing tissue in medical imaging.

FIG. 3 shows an example using manually programmed features. One or more images are acquired from memory or directly from a scanner. The textural features are extracted from the images. The values of the features are used for classification to provide outcomes.

In another embodiment, deep-learnt features are used. The values are extracted from frames of data for features learned from machine learning. Deep machine learning learns features represented in training data as well as training the classifier rather than just training the classifier from the manually designated features.

Figure 4:
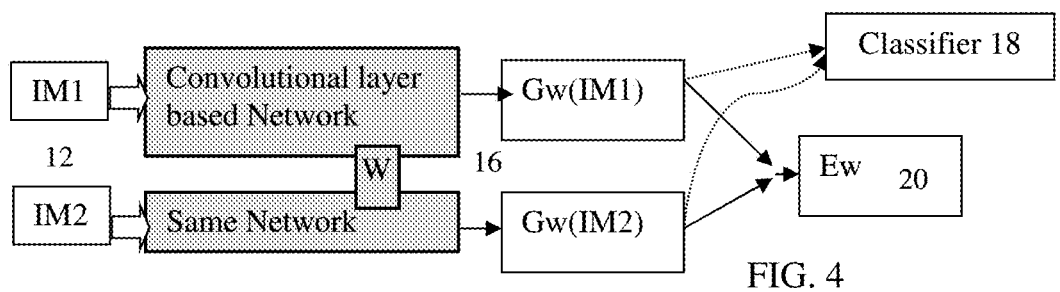
FIG. 4 is a flow chart diagram of a deep-learning embodiment of the method for characterizing tissue in medical imaging.

Any deep learning approach or architecture may be used. In one embodiment, the extracting and classifying of acts 16 and 18 are based on a twin or Siamese convolution network. FIG. 4 shows an example for deep learning. The twin or Siamese convolutional networks are trained to extract features from given multi-modal, multi-dimensional images, IM1 and IM2, such as multi-modal frames representing pre and post treatment, respectively. The relevant features are automatically determined as part of training. This ability allows for the generic training on arbitrary data (i.e., training data with known outcomes) that can internally determine features, such as textures. The Siamese convolution networks are linked so that the same weights (W) for the parameters defining the networks are used in both branches. The Siamese network uses two input images (e.g., one branch for pre-treatment and another branch for post-treatment). Kernels weights for convolution are learnt using both branches of the network, and optimized to provide values to Gw.

The Siamese deep learning network is also trained to classify small, large or absence of changes between time points. The definition of such features is based on a specific loss function Ew that minimizes difference between time points when there is no or small changes and maximizes the differences when there are large changes between them. The features indicating relevant differences between the two inputs are learned from the training data. By training the network with labeled outcomes, the network learns what features are relevant or can be ignored for determining the prognosis, diagnosis, or finding similar cases. During training, low-level features and invariants are learned by the convolutional networks that have exactly the same parameters. These networks determine the core feature set that differs between the two input datasets based on feedback during learning of the difference network.

Figure 5:
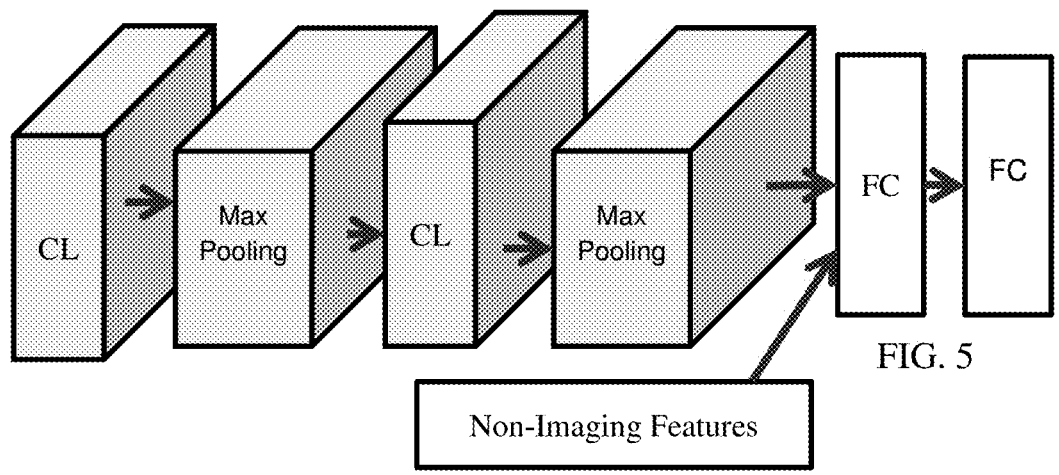
FIG. 5 is an example of a deep-learning convolution layer-based classification network incorporating non-imaging features.

FIG. 5 shows an example convolution layer-based network for learning to extract features. Each branch or twin has the same layers or network structure. The networks themselves are shown as layers of convolutional, sub-sampling (e.g., max pooling), and fully connected layers. By using convolution, the number of possible features to be tested is limited. The fully connected layers (FC) in FIG. 5 operate to fully connect the features as limited by the convolution layer (CL) after maximum pooling. Other features may be added to the FC layers, such as non-imaging or clinical information. Any combination of layers may be provided. Additional, different, or fewer layers may be provided. In one alternative, a fully connected network is used instead of a convolution network.

Returning to FIG. 4, the two parallel networks process the pre and post therapy data, respectively. The networks are trained with exactly the same parameters in the Siamese network. The features that optimally discriminate based on the loss function, Ew, are automatically developed during training of the network. For example, the multi-modal input frames are for T2 and ADC for each time. The features related to textural information for the T2 image and local deviations in the ADC image highlighting the differences from pre and post treatment are learned. These learnt features are then applied to frames of data for a specific patient, resulting in Gw values for the specific patient.

In act 18 of FIG. 1, the machine-learnt classifier classifies the tissue of the patient from the extracted values of the features. The values are input to the machine-learnt classifier implemented by the processor. By applying the classifier, the tissue is classified. For example, a therapy response of the tissue in the tissue region is classified from the values of the features as input to the machine-learnt classifier.

In the approach of FIG. 3, any machine-learnt classifier may be used. The classifier is trained to associate the categorical labels (output) to the extracted values of one or more features. The machine-learning of the classifier uses training data with ground truth, such as values for features extracted from frames of data for patients with known outcomes, to learn to classify based on the input feature vector. The resulting machine-learnt classifier is a matrix for inputs, weighting, and combination to output a classification. Using the matrix or matrices, the processor inputs the extracted values for features and outputs the classification.

Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used.

In one embodiment, the classification is by a machine-learnt classifier learnt with the deep learning. As part of identifying features that distinguish between different outcomes, the classifier is also machine learnt. For example in FIG. 4, the classifier 18 is trained to classify the tissues based on the feature values Gw, obtained from a Siamese network that is already optimized/trained to maximize differences of images from different categories and minimize differences of images from the same categories. For example, the classifier categorizes the tumor from the feature values, such as classifying a type of tumor, a tumor response to therapy, or other tissue characteristic. In the example of FIG. 4, the classification is based on features from Gw, which are optimized from the loss Ew. First, the Siamese network trains and/or defines kernels such that the feature vectors Gw can help discriminate for all categories. Once, the network is trained, the classifier 18 uses Gw and then defines probabilities that two images from different time points have zero, small or large differences.

In either approach (e.g., FIG. 3 or FIG. 4), additional information may be used for extracting and/or classifying. For example, values of clinical measurements for the patient are used. The classifier is trained to classify based on the extracted values for the features in the frames of data as well as the additional measurements. Genetic data, blood-based diagnostics, family history, sex, weight, and/or other information are input as a feature for classification.

The classifier is trained to classify the tumor. The classifier is trained to classify the tissue into one of two or more classes. By inputting extracted values for a specific patient, the machine-learnt classifier classifies the tumor for that patient into one of the classes. Any of various applications may be used.

Figure 6:
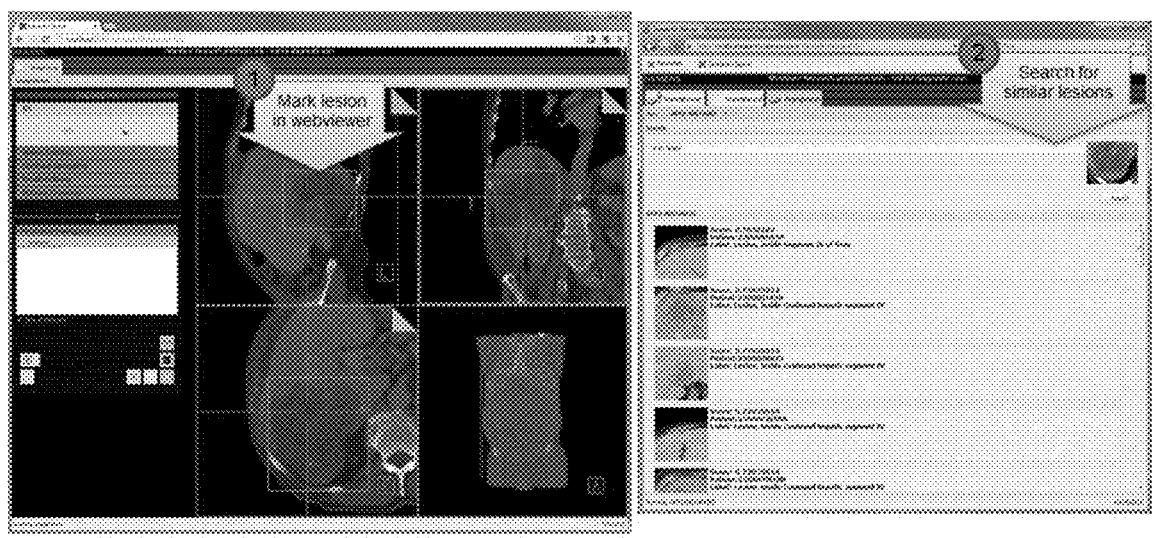
FIG. 6 illustrates an example output of a related case identified through classification.

In one embodiment, the classifier identifies a similar case. The similar case includes an example treatment and outcome for another patient with a tissue region similar to the tissue region of the current patient. Any number of these reference cases may be identified. A database of possible reference cases is used. The most similar case or cases to the current patient are identified by the classifier. Using the extracted values for texture features with or without other features, the classifier identifies the class as a reference case or cases. In evidence-based medicine, decision-making is optimized by emphasizing the use of evidence from well designed and conducted research. One key component is to retrieve the evidence in the form of other cases using the current case. For example, as in FIG. 6, once a lesion is marked by the user, the values for the textural features are extracted and used by the classifier to retrieve the closest cases. These closest cases provide the evidence, such as a list of similar cases with thumbnail images of the tumors for the reference cases.

Another class is therapy response. The success or failure of therapy is predicted as a diagnosis or prognosis. In an alternative, rather than binary indication of success or failure, a range providing an amount and/or probability of success or failure is output as the class. Whether the patient is likely to respond (i.e., responder), not likely to respond (i.e., non-responder), or may partially respond (i.e., partial or semi-responder) is output. The predicted survival time of the patient may be the output.

Figure 7:
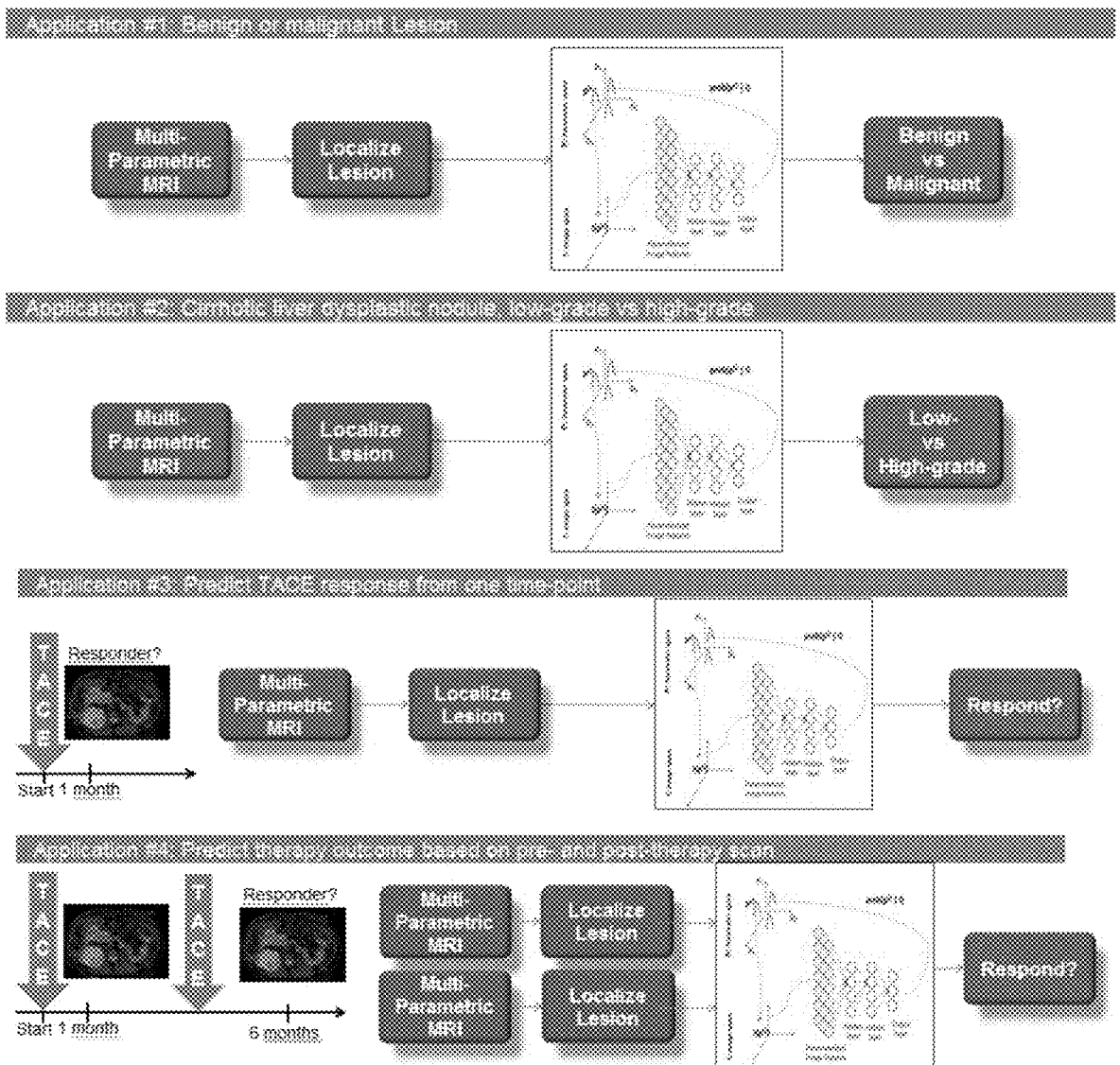
FIG. 7 illustrates four example applications of machine-learnt classification of tissue characteristics.

FIG. 7 shows two examples of classifying the tissue as successful or not successful therapy. In applications #3 and #4, the therapy response of the tumor is classified. A trans arterial chemo embolization (TACE) is used as the example therapy. In application #3, multi-parametric (e.g., T2 and ADC) data for one time (e.g., 1 month after treatment) is used. After identifying the tissue region of interest for the tumor, the classification is applied to determine whether the tumor is responding to the treatment. The level or rate of response may be output, informing a decision on any continued treatment and level of treatment. In an alternative, treatment is not applied. The frames of data prior to treatment are used to classify whether the treatment is expected to be successful based on the extracted textural and/or other features prior to treatment.

In application #4, multiple treatments are performed. Frames of data after each treatment are used. The response of the tumor is measured or predicted based on the classification from the data over time. In an alternative, only the second treatment is performed and the first frames of data at 1 month are pre-treatment frames. The features from the different times are used to predict or measure therapy response.

Figure 8A:
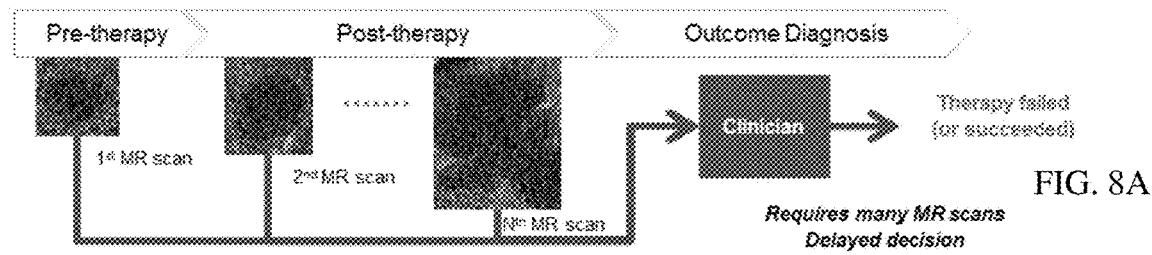
FIG. 8A shows an example time line for measuring therapy response relying on trending over many times post treatment.
Figure 8B:
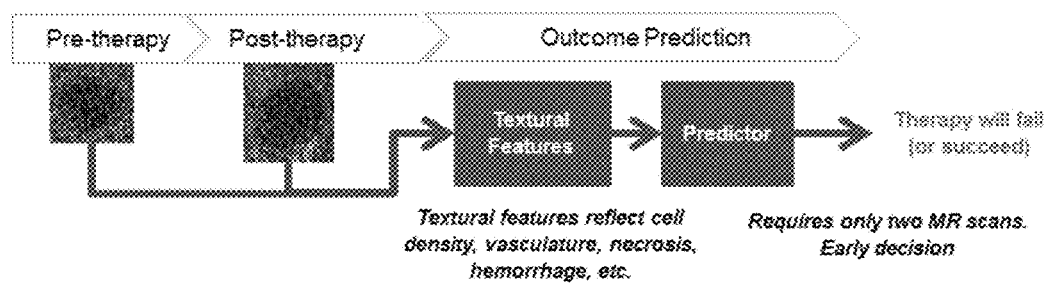
FIG. 8B shows an example time line for measuring the therapy response relying on measurement for just one time post treatment.

By inferring the therapy success or level of success for therapy applied to the tissue region, a decision on whether to continue therapy and/or to change the therapy may be more informed and/or performed earlier. FIG. 8A shows an example of predicting therapy outcome. In this example, RECIST is used, so the size change of the tumor is measured N times post-therapy. Eventually, a sufficient trend is determined by the clinician to predict the outcome. FIG. 8B shows an alternative approach using the machine-learnt classifier. Less information is needed, such as just one set of post therapy frames of data (e.g., from one time or appointment for scanning). With textural and/or other feature analysis and machine-learnt classification, the therapy success or failure decision may be inferred without manual perception of trends. A lesser number of scans and lesser amount of time are needed to make therapy decisions. The success of the therapy applied to the tumor is inferred and used to optimize treatment.

Other classes for machine-learnt classification may be used. The classifier may be machine trained to classify the tumor (e.g., suspicious tissue region) as benign or malignant. Once the lesion is segmented or identified, values for textural features are computed for the lesion. The values are fed into the machine-learnt classifier for labeling of malignancy.

The classifier may be trained to output values for staging the tumor. Using advanced tissue characterization provided by the machine-learnt classifier, the stage is output. For example in liver tissue, the extracted textural features are used by the classifier to output a measure of fibrosis staging. In other examples, the classifier is trained to output tags used for staging, such as outputting the measures used for staging the tumor. The values for the features are used by the classifier to provide the tag or staging measure. In quantitative BIRADS for beast examination, the textural features are extracted, and then the classifier associates the categorical labels of clinically descriptive tags (e.g., measures of mass, symmetry, and non-mess-like enhancement) to the extracted features. The inferred tags are then used to manually or automatically stage the breast tumor. In quantitative PIRADS for prostate examination, the textural features are extracted, and then the classifier associates the categorical labels of clinically descriptive tags (e.g., tags for the peripheral zone, central zone, and transition zone) to the extracted features. The inferred tags are then used to manually or automatically stage the prostate.

In another embodiment, the classifier is trained to output any information useful for diagnosis or prognosis. For example, information to enhance therapy monitoring is output. An intensity histogram, histogram of difference over time in the intensities representing the tumor, and/or a difference of histograms of intensities representing the tumor at different times are calculated and output without the classifier. The classifier supplements these or other image intensity statistics or histograms. Information derived from the textual features and/or other features is used to provide any information useful to clinicians.

More than one machine-trained classifier may be used. The same or different features are used by different classifiers to output the same or different information. For example, a classifier is trained for predicting therapy response, and another classifier is trained to output tags for staging. In alternative embodiments, one classifier is trained to output different types of information, such as using a hierarchal classifier.

FIG. 7 shows four example use cases of classification using multi-parametric magnetic resonance frames of data. "Localize Lesion" represents identifying a tissue region of interest (ROI) by segmentation or by user region designation (e.g., act 14). In applications #1, #2, and #3, the input to the system is a set of multi-parametric magnetic resonance images from a single time point, and the system performs one or more of three different tasks: in application #1, the task is to predict whether the tumor is benign or malignant. The outcome may be either discrete (e.g., Yes vs No) or continuous (e.g., giving an indication of the severity of the malignancy, such as a number between 0 and 1). In application #2, the task is to predict whether the tumor is low- or high-grade. The grading may be discrete (e.g., Low vs High) or continuous (e.g., a number between 0 to the N, where N is the highest grade possible). In application #3, the task is to predict whether the patient responds to the therapy. The response may be discrete (e.g., responding vs not-responding) or continuous (a number indicating the degree of response, such as between 0 and 1). In application #4, the input to the system is a set of multi-parametric magnetic resonance images from two or more time points, and the system performs the same task as in applications #3, which is to predict the response, based on the values extracted from each of the images.

In act 20 of FIG. 1, the tissue classification is transmitted. Any of the tissue classifications output by the classifier are transmitted. Alternatively, information derived from the output of the classification is transmitted, such as a stage derived from classification of tags.

The transmission is to a display, such as a monitor, workstation, printer, handheld, or computer. Alternatively or additionally, the transmission is to a memory, such as a database of patient records, or to a network, such as a computer network.

The tissue classification is output to assist with prognosis, diagnosis, or evidence-based medicine. For example, a list of similar patients, including their treatment regime and outcome, is output. As another example, a predicted therapy response is output in a report for the patient.

The tissue classification is output as text. An image of the tumor is annotated or labeled with alphanumeric text to indicate the classification. In other embodiments, an image of the tissue is displayed, and the classification is communicated as a symbol, coloring, highlighting or other information added onto the image. Alternatively, the classification is output in a report without the image of the tumor or separated (e.g., spaced away) from the image of the tumor.

The tissue may also be classified very locally (e.g., independent classification of every voxel). The resulting classification is output as a colored or highlighted overlay onto images of the tissue, visually indicating, spatially, possible regions of likely response or non-response.

Other information may be output as well. Other information includes values for the features, clinical measures, values from image processing, treatment regime, or other information (e.g., lab results).

Figure 9:
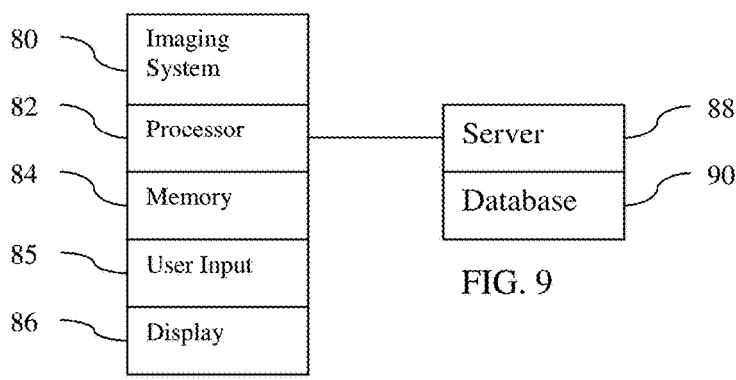
FIG. 9 is one embodiment of a system for tissue characterization in medical imaging.

FIG. 9 shows a system for tissue characterization in medical imaging. The system includes an imaging system 80, a memory 84, a user input 85, a processor 82, a display 86, a server 88, and a database 90. Additional, different, or fewer components may be provided. For example, a network or network connection is provided, such as for networking with a medical imaging network or data archival system. In another example, the user input 85 is not provided. As another example, the server 88 and database 90 are not provided. In other examples, the server 88 connects through a network with many imaging systems 80 and/or processors 82.

The processor 82, memory 84, user input 85, and display 86 are part of the medical imaging system 80. Alternatively, the processor 82, memory 84, user input 85, and display 86 are part of an archival and/or image processing system, such as associated with a medical records database workstation or server, separate from the imaging system 80. In other embodiments, the processor 82, memory 84, user input 85, and display 86 are a personal computer, such as desktop or laptop, a workstation, a server, a network, or combinations thereof. The processor 82, display 86, user input 85, and memory 84 may be provided without other components for acquiring data by scanning a patient.

The imaging system 80 is a medical diagnostic imaging scanner. Ultrasound, computed tomography (CT), x-ray, fluoroscopy, positron emission tomography, single photon emission computed tomography, and/or magnetic resonance (MR) systems may be used. The imaging system 80 may include a transmitter and includes a detector for scanning or receiving data representative of the interior of the patient.

In one embodiment, the imaging system 80 is a magnetic resonance system. The magnetic resonance system includes a main field magnet, such as a cryomagnet, and gradient coils. A whole body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing. Anatomical and/or functional scanning sequences may be used to scan the patient, resulting in frames of anatomical and/or functional data representing the tissue.

The memory 84 may be a graphics processing memory, a video random access memory, a random access memory, system memory, cache memory, hard drive, optical media, magnetic media, flash drive, buffer, database, combinations thereof, or other now known or later developed memory device for storing data or video information. The memory 84 is part of the imaging system 80, part of a computer associated with the processor 82, part of a database, part of another system, a picture archival memory, or a standalone device.

The memory 84 stores medical imaging data representing the patient, segmentation or tissue region information, feature kernels, extracted values for features, classification results, a machine-learnt matrix, and/or images. The memory 84 may alternatively or additionally store data during processing, such as storing seed locations, detected boundaries, graphic overlays, quantities, or other information discussed herein.

The memory 84 or other memory is alternatively or additionally a non-transitory computer readable storage medium storing data representing instructions executable by the programmed processor 82 for tissue classification in medical imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The user input 85 is a keyboard, mouse, trackball, touch pad, buttons, sliders, combinations thereof, or other input device. The user input 85 may be a touch screen of the display 86. User interaction is received by the user input, such as a designation of a region of tissue (e.g., a click or click and drag to place a region of interest). Other user interaction may be received, such as for activating the classification.

The processor 82 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for segmentation, extracting feature values, and/or classifying tissue. The processor 82 is a single device or multiple devices operating in serial, parallel, or separately. The processor 82 may be a main processor of a computer, such as a laptop or desktop computer, or may be a processor for handling some tasks in a larger system, such as in an imaging system 80. The processor 82 is configured by instructions, design, hardware, and/or software to perform the acts discussed herein.

The processor 82 is configured to perform the acts discussed above. In one embodiment, the processor 82 is configured to identify a region of interest based on user input, extract values for features for the region, classify the tumor in the region (e.g., apply the machine-learnt classifier), and output results of the classification. In other embodiments, the processor 82 is configured to transmit the acquired frames of data or extracted values of features to the server 88 and receive classification results from the server 88. The server 88 rather than the processor 82 performs the machine-learnt classification. The processor 82 may be configured to generate a user interface for receiving seed points or designation of a region of interest on one or more images.

The display 86 is a monitor, LCD, projector, plasma display, CRT, printer, or other now known or later developed devise for outputting visual information. The display 86 receives images, graphics, text, quantities, or other information from the processor 82, memory 84, imaging system 80, or server 88. One or more medical images are displayed. The images are of a region of the patient. In one embodiment, the images are of a tumor, such as three-dimensional rendering of the liver with the tumor highlighted by opacity or color. The image includes an indication, such as a text, a graphic or colorization, of the classification of the tumor. Alternatively or additionally, the image includes a quantity based on the classification, such as a tag value. The quantity or classification output may be displayed as the image without the medical image representation of the patient. Alternatively or additionally, a report with the classification is output.

The server 88 is a processor or group of processors. More than one server 88 may be provided. The server 88 is configured by hardware and/or software to receive frames of data (e.g., multi-parametric images), extracted features from frames of data, and/or other clinical information for a patient, and return the classification. The server 88 may extract values for the features from received frames of data. To classify, the server 88 applies a machine-learnt classifier to the received information. Where the classification identifies one or more reference cases similar to the case for a given patient, the server 88 interacts with the database 90.

The database 90 is a memory, such as a bank of memories, for storing reference cases including treatments for tumor, frames of data and/or extracted values for features, and outcomes for evidence-based medicine. The server 88 uses the database 90 to identify the cases in the database most or sufficiently similar to a current case for a current patient. The server 88 transmits the identity of the reference and/or the reference information to the processor 82. In alternative embodiments, the server 88 and database 90 are not provided, such as where the processor 82 and memory 84 extract, classify, and output the classification.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for tissue characterization in medical imaging, the method comprising:

scanning a patient with a medical scanner, the scanning providing multiple frames of data representing a tissue region of interest in the patient;

extracting, by a processor, values for features from the frames of data, the features comprising deep-learnt features from deep learning based on Siamese convolution networks;

classifying, by a machine-learnt classifier learnt with the deep learning based on the Siamese convolution networks and implemented by the processor, a therapy response of the tissue of the tissue region from the values of the features as input to the machine-learnt classifier; and transmitting the therapy response.

2. The method of claim 1 wherein scanning comprises scanning with a magnetic resonance scanner, computed tomography scanner, ultrasound scanner, positron emission tomography scanner, single photon emission computed tomography scanner, or combinations thereof.

3. The method of claim 1 wherein scanning comprises scanning with a magnetic resonance scanner, the frames of data comprising functional measurements by the magnetic resonance scanner.

4. The method of claim 1 wherein extracting values comprises extracting the values as scale-invariant feature transformation, histogram of oriented gradients, local binary pattern, gray-level co-occurrence matrix, or combinations thereof.

5. The method of claim 1 wherein classifying comprises classifying from the values of the features extracted from the frames of data and values of clinical measurements for the patient.

6. The method of claim 1 wherein scanning comprises scanning at different times, different contrasts, or different types, the frames corresponding to the different times, contrasts, or types, and wherein classifying comprises classifying the therapy response based due to differences in the frames.

7. The method of claim 1 wherein classifying the therapy response comprises inferring therapy success for therapy applied to the tissue region.

8. The method of claim 1 wherein classifying the therapy response comprises identifying an example treatment and outcome for another patient with similar extracted values of the features.

9. The method of claim 1 wherein transmitting the therapy response comprises displaying the therapy response in a report.

10. The method of claim 1 further comprising identifying, by a user input device responsive to user selection, the tissue region, wherein the extracting, classifying, and transmitting are performed without user input after the identifying.

11. The method of claim 1 wherein the extracting and classifying are performed by the processor remote from the medical scanner.

12. The method of claim 1, where therapy response comprises a responder classification, non-responder classification, or a prediction of survival time.

13. The method of claim 1 wherein transmitting the therapy response comprises displaying the therapy response as an overlay over images of the tissue region.

14. A method for tissue characterization in medical imaging, the method comprising:

scanning a patient with a medical scanner, the scanning providing different frames of data representing different types of measurements for tissue in the patient; extracting, by a processor, values for features from the frames of data, the values being for features that are deep-learnt features from deep learning based on Siamese convolution networks; classifying, by a machine-learnt classifier learnt with the deep learning based on the Siamese convolution networks and implemented by the processor, the tissue of the patient from the values of the features as input to the machine-learnt classifier, the machine-learnt classifier being a deep-learnt classifier, the deep-learnt features and deep-learnt classifier being performed on the Siamese convolution networks; and transmitting the tissue classification.

15. The method of claim 14 wherein scanning comprises scanning with a magnetic resonance scanner, the different types of measurements including an apparent diffusion coefficient.

16. The method of claim 14 wherein extracting comprises extracting the values for a texture of the tissue represented by at least one of the frames of data.

17. The method of claim 14 wherein classifying the tissue comprises classifying a predication of response of the tissue to therapy, classifying a benign or malignant, classifying a staging tag, a similarity to a case, or combinations thereof.

18. A method for tissue characterization in medical imaging, the method comprising:
scanning a patient with a medical scanner, the scanning providing a frame of data representing a tumor in the patient;
extracting, by a processor, values for deep-learnt features from the frame of data;
classifying, by a deep-machine-learnt classifier implemented by the processor, the tumor from the values of the features as input to a machine-learnt classifier; and
transmitting the classification of the tumor;
wherein the deep-learnt features and the deep-machine-learnt classifier are from a Siamese convolution network.

* * * * *